United States Patent [19]

Ashmead et al.

[11] Patent Number: 5,614,553

[45] Date of Patent: Mar. 25, 1997

[54] COMPOSITION AND METHOD FOR ALLEVIATING STRESS IN WARM-BLOODED ANIMALS

[75] Inventors: H. DeWayne Ashmead, Fruit Heights; Harvey H. Ashmead, Kaysville; Robert B. Jeppsen, Layton, all of Utah

[73] Assignee: Albion Laboratories, Inc., Clearfield, Utah

[21] Appl. No.: 839,828

[22] Filed: Feb. 21, 1992

Related U.S. Application Data

[63] Continuation-in-part of Ser. No. 549,112, Jul. 6, 1990, Pat. No. 5,162,369.

[51] Int. Cl.$^6$ ..................................................... A61K 31/28
[52] U.S. Cl. ........................................... 514/505; 514/492
[58] Field of Search .................................... 514/492, 505, 514/494, 499, 502

[56] References Cited

PUBLICATIONS

Nutrition Research 1981. 1(6):617–622.Shah.
Biol Trace Elem Res Jul.–Dec. 1990, 26–27 pp. 599–611. Nielsen.

*Primary Examiner*—Zohreh Fay
*Attorney, Agent, or Firm*—Thorpe, North, & Western, L.L.P.

[57] ABSTRACT

A method for alleviating stress and/or stress related symptoms in humans and other warm-blooded animals particularly when such symptoms are complicated by intestinal malabsorption of minerals is disclosed. Chromium and, optionally, one or more other minerals selected from the group consisting of copper, zinc, manganese, iron and selenium are provided in the form of amino acid chelates having a ligand to mineral ratio of at least 1:1, a molecular weight of no more than 1500 and a stability constant of between about $10^6$ and $10^{16}$ and administered orally. They are absorbed from a portion of the intestinal tract other than that utilized for the absorption of cations. The method is particularly adapted to reducing and/or controlling levels of serum cortisol in humans or other animals. The presence of symptoms of stress may first be confirmed or the compositions may be administered as a prophylactic.

20 Claims, No Drawings

5,614,553

COMPOSITION AND METHOD FOR ALLEVIATING STRESS IN WARM-BLOODED ANIMALS

This application is a continuation-in-part of application Ser. No. 549,112, filed Jul. 6, 1990 now U.S. Pat. No. 5,162,369.

BACKGROUND AND FIELD OF THE INVENTION

This invention relates to compositions and methods of alleviating stress and stress related disease in humans and other warm-blooded animals. More particularly, this invention relates to amino acid chelated mineral compositions containing chromium and, optionally, one or more minerals selected from the group consisting of copper, zinc, manganese, iron and selenium and to methods of administering these compositions to influence mineral uptake and absorption in humans and other warm-blooded animals subjected to conditions of stress or exhibiting symptoms of stress.

Stress may be brought on by many factors of which strenuous exercise, physical training, change in environment, infection, dietary irregularity (e.g. elevated glucose and/or low protein intake), increased urinary excretion of chromium and other essential minerals are only exemplary. Conditions of stress in warm-blooded animals may be indicated by a variety of overt symptoms or signs. General malaise, increased morbidity and/or mortality, poor food conversion and/or loss of weight and sterility, among others, are indications of stress. Most forms of stress and disease result in some reduction in feed intake.

In copending application Ser. No. 549,112, it was reported that deficiencies in such minerals as copper, zinc, manganese, iron and selenium could result in increased morbidity and/or reduced immune response. It is reported that zinc deficiency may decrease insulin secretion, increase insulin resistance and/or reduce insulin action. Zinc and copper have also been shown to influence immune response in ruminants and other animals. See Bull, *Trace Minerals and Immunology*, Western Nutritional Conference, 1990, Gershwin et al., *Trace Element Deficiencies and Immune Responsiveness*, Trace Elements in Man and Animals (Ed. L. S. Hurley) Plenum Press. N.Y., 1988. Zinc, copper and manganese are the most common trace minerals influencing enzyme systems controlling proper immune functions, Lente, *Copper Proteins and Copper Enzymes*, Vol. 11, CRC Press, Boca Raton. Fla., 1984. Manganese plays a critical role in carbohydrate metabolism including a requirement in insulin synthesis and release, Gershwin et al., supra. Evidence also suggests that deficiencies in many of the micronutrients such as zinc, copper, chromium and manganese, as well as vitamin B-6, may lead to glucose intolerance.

Chromium functions as a potentiator of insulin. Chromium is a trivalent mineral which has been found in recent years to be more bioavailable when administered as an organic complex. The most common organic complex is a low-molecular weight organic complex termed "glucose tolerance factor" (GTF) obtained primarily from Brewer's yeast. Recent research has shown that various stressors such as infection, strenuous exercise, pregnancy, change of environment, etc, increase urinary excretion of chromium. Suboptimal levels of chromium may be a factor in several stress related diseases. Schnauzer et al., *Effects Of Chromium Supplementation in Food Energy Utilization and the Trace-element Composition in the Liver and Heart of Glucose-exposed Young Mice*, Biol. Trace Element Res. 9:79 1986, have shown that chromium supplementation protects against stress-induced losses of trace minerals such as zinc, copper, iron and manganese. Polansky et al., *Beneficial Effects of Supplemental Chromium on Glucose, Insulin and Glucagon of Subjects Consuming Controlled Low Chromium Diets*, FASEB J. A2964. 1990, report that human dietary chromium intakes is suboptimal with diets of approximately twenty-five percent of the U.S. population containing forty percent or less of the recommended daily chromium intake. There is also evidence that chromium in the human body decreases with age. In the animal kingdom, it has been found that steers, subjected to conditions of stress, have increased serum cortisol levels which can be lowered by administration of supplemental chromium.

One particular form of stress in cattle is bovine respiratory disease complex (BRD), also known as "shipping fever". Despite improvements in management feeding and vaccines, a high incidence of this disease still exists and remains one of the most important syndromes affecting the health status of cattle in feedlots, particularly in those feeding calves. BRD is often present in combination with viral and bacterial pathogens which only add to the problems. Buyers continue to suffer the associated loses of shrinkage, treatments costs, inefficient gain and occasional death. The magnitude of these losses and the public concern about indiscriminant use of antibiotics make it imperative that better methods be developed to control this disease complex.

Recent research, particularly with monogastric animals, has shown beneficial effects of various nutrients on immunocompetence and consequent resistance to infectious agents. For example, it has been shown that administration of chromium, tends to suppress the effects of BRD when administered to feeder calves. Chromium supplementation has demonstrated increased weight gain and reduced morbidity in studies carried out in calves shipped from a distant location to a feed lot.

Moreover, chromium is an essential trace element as a co-factor in several enzyme systems. As mentioned above, it is associated with a low-molecular weight organic complex termed "glucose tolerance factor" (GTF) that acts with insulin in promoting normal glucose utilization. Brewer's yeast, which is rich in GTF, has been shown to improve glucose tolerance, lower serum cholesterol and triglycerides in some subjects and to reduce insulin requirements in some diabetics. Glucose tolerance is usually impaired in protein-calorie malnutrition and some cases have shown a dramatic response to administration of trivalent chromium. Deficiency has been reported in patients on prolonged parenteral feeding. Additionally, GTF is not only a co-factor of insulin thus influencing glucose, but protein and lipid metabolism as well. GTF is not as effective, if not ineffective, in the absence of insulin. The exact mechanism by which GTF improves glucose tolerance is not known. However, it is thought that GTF enhances the binding of insulin to its specific receptors.

Elevated cortisol levels are known to suppress the immune system. Cortisol prevents glucose entry into muscle and adipose tissue and decreases activity of insulin. Moreover, cortisol has been shown to inhibit LH release in the bovine species and therefore has an effect on reproduction. Insulin availability may limit the onset of ovarian activity leading to first ovulation. Insulin is also known to reduce concentration of blood ketone bodies. Supplemental chromium, when used to decrease serum cortisol, in dairy cows may increase milk production. Sartin et al., *Plasma Concentrations of Metabolic Hormones in High and Low Pro-* ducing Dairy Cows, J. Dairy. Sci. 71:650–657, 1988 reports that cortisol is antagonistic to milk production. Supplemental chromium also has been found to be associated with weight gain in stressed animals. Part of the improvement in gain with administering supplemental chromium may be due to decreasing cortisol production. It has been shown by Southorn et al., *The Effect of Corticosterone Treatment of the Response of Muscle protein Synthesis to Insulin Infusion in the Rat*, J. Endocrin. 23:abst. #127, 1989, that rats treated with corticosterone developed insulin resistance with respect to muscle protein synthesis. Clinical evidence supports the immunosuppressive activity of glucocorticoids through impairment of neutrophil function and suppression of lymphocyte blastogenesis.

Another part of the beneficial effects of chromium on the immune system may be related to vitamin C metabolism. It is known that cattle arriving at a feedlot in a chronically stressed condition show evidence of hyperglycemia and are at greater risk of disease as vitamin C entry into neutrophils is most likely reduced. Vitamin C is needed for neutrophil function, decreases circulating corticoid levels and ameliorates immunosuppression in stress. Nockels, *Effect of Stress on Mineral Requirements*, Western Nutritional Conference, 1990 and Satterlee et al., *Vitamin C Amelioration of the Adrenal Stress Response in Broiler Chickens Being Prepared for Slaughter*, Comp. Biochem. Physiol., 94A:569–574, 1989 have shown that vitamin C ameliorates the negative effect of stress in broiler chickens being prepared for slaughter which is possibly due to suppression of adrenocortical steroidogenesis. Synthesis of ascorbate from glucose may be reduced when glucose is deficient as in earlier fasting during transport. Calves may also have a low glucose synthesis when fed forage diets so vitamin C synthesis may be low.

Glucocorticoids are known to suppress the immune system according to Munck et al, *Physiological Functions of Glucocorticoids in Stress and Their Relation to Pharmacological Actions*, Endoc. Rev. 5:25, 1984. Therefore, another beneficial effect of chromium supplementation during periods of stress in suppressing cortisol serum levels could conceivable result in improving effectiveness of certain vaccines. Carlson et al., *The Bovine Proceedings*, 15:84 1990, measured antibody response to IBR vaccination in feedlot cattle found cattle to be poorly responsive to immunization upon arrival in the feedlot. These results were attributed to the stresses of shipping and respiratory infection drawing the conclusion that such factors may render an animal immunocompetent.

Once chromium is mobilized in response to increased glucose metabolism and/or elevated insulin response, it is not reabsorbed in the tissues but is excreted in the urine. Therefore, diets that lead to elevated circulating insulin will lead to chromium depletion.

As shown by U.S. Pat. No. 4,954,492, there have been numerous attempts to prepare synthetic trace metal complexes which exhibit GTF activity to mimic or enhance the GTF activity found in Brewer's yeast. This research has primarily centered around the use of chromium complexed with nicotinic acid and amino acids.

In addition to conditions of metabolic stress, viral and other infections sometimes overwhelm the immune system leading to secondary complications which tend to exacerbate the primary stress symptoms. For example, some infections cause morphological changes in the intestine which result in malabsorption which may hinder the uptake of essential trace minerals and/or the metallic co-factors which are beneficial for immune system functioning. A common site of intestinal abnormality is the duodenum, the portion of the small intestine where metal ions are primarily absorbed under normal conditions. Since the pH in the duodenum is acidic, metal ions are present in soluble ionic form. As these ions pass along the intestinal tract, the Ph in the jejunum becomes more basic and absorption of metals in ionic form becomes more difficult. Diarrhea is also a common problem associated with many infections due to the profuse fluid secretion in the duodenum and proximal jejunum resulting in malabsorption of minerals.

One factor which may contribute to the malabsorption of minerals, exacerbated by conditions of stress, is that ionic mineral absorption requires an integral protein carrier molecule embedded in and transversing the mucosal membrane. Once absorbed into the mucosal cell the transfer of the cation from the terminal web below the microvilli to the basement membrane requires the presence of carrier proteins. For iron and most minerals apoferritin is a suitable carrier. In the case of zinc, albumin is the carrier protein. For copper the carrier is ceruloplasmin and for manganese it is transmanganin. If, due to stress or lack of proper mineral availability, the metabolic system of an animal is suppressed or does not function properly the chemistry of the cells is altered and the cells do not perform their tasks due to mineral deficiencies.

From the above it is evident proper metabolic functioning of chromium and also other minerals such as copper, zinc, manganese, iron and selenium are known to play an important role in maintaining the health and vigor of an animal. Moreover, it is also evident that there may be metabolic dysfunctioning of cells on the surface of the intestinal lumen to the point that these minerals may not be adequately absorbed in warm-blooded animals, including humans. This could occur if the animal were suffering from conditions of stress which affected the portion of the intestine where mineral ions were most likely to be absorbed, i.e. the duodenum. Over a period of time, the inability of the body to absorb these minerals would result in compromising proper metabolic functioning and allowing secondary diseases to be introduced into the body. It would therefore be beneficial to provide chromium and, if desired, other essential minerals to warm-blooded animals subjected to conditions of stress and/or exhibiting symptoms of metabolic dysfunctioning known to be brought on by stress in a bioavailable form in which such minerals would be absorbed via a pathway which did not require duodenal absorption in ionic form.

Ashmead et al., U.S. Pat. No. 4,020,158; Ashmead, U.S. Pat. No. 4,076,803; Jensen U.S. Pat. No. 4,167,564; Ashmead, U.S. Pat. No. 4,774,089 and Ashmead, U.S. Pat. No. 4,863,898 all teach various uses for amino acid chelates in reference to increasing absorption of essential minerals into biological tissues. Some of these patents suggest that certain mineral and ligand combinations can enhance metal uptake in specific organs or tissues where specific biological functions are enhanced, i.e. minerals crossing the placental membranes into foeti, estrus or spermatogenesis, etc. However, it has not heretofore been known that administration of chromium, in chelated form, administered alone or in combination of other metal amino acid chelates can have a positive effect in reducing serum cortisol levels and otherwise alleviating conditions of stress.

OBJECTS AND BRIEF SUMMARY OF THE INVENTION

It is an object of the present invention to provide to a human or other warm-blooded animal, negatively affected by a form of stress, with chromium and, optionally, with one or more trace minerals selected from the group consisting of copper, zinc, manganese, iron and selenium in such quantities and ratios as are required to minimize or alleviate the conditions of stress.

It is also an object of the present invention to provide a method of minimizing symptoms of stress in warm-blooded animals exacerbated by intestinal malabsorption of minerals by means of administering to said animals, sufficient minerals, including chromium, in a bioavailable form which can be absorbed from a portion of the intestinal tract other than the duodenum through the utilization of a different pathway for their uptake, rather than the pathway employed by cations.

An additional object of this invention is to provide a means of maintaining optimal chromium levels to function as a co-factor with insulin and control levels of serum cortisol.

These and other objects may be accomplished by the proper formulation of chromium and, optionally, one or more additional essential minerals selected from the group consisting of copper, zinc, manganese, iron and selenium and the administration of chromium, and such other minerals, if desired, to a warm-blooded animal subjected to stress and/or showing symptoms of stress, particularly when exacerbated by intestinal mineral malabsorption. By proper formulation is meant the providing of chromium and such other minerals in a form which is bioavailable to the animal at intestinal absorption sites other than those utilized strictly for cationic absorption. Also, the amount or chromium administered and the ratio of chromium to the other minerals and even the ratio of one mineral to another may be significant and can vary depending upon the species of animal and the form and/or stage of stress.

Bioavailable forms of chromium, copper, zinc, manganese, iron and selenium which are absorbed via the intestinal tract of a warm-blooded animal at a site other than the cation absorption sites in the duodenum are those made by chelating the mineral with an amino acid or peptide ligand wherein the ligand to mineral ratio is at least 1:1 and preferably 2:1 or higher and wherein the molecular weight of the amino acid chelate formed is not greater than 1500 and preferably does not exceed 1000. Such amino acid chelates are stable and are generally absorbed intact through the intestinal tract via active dipeptide transport. Such amino acid chelates have a stability constant of between about $10^6$ and $10^{16}$. A more detailed description of such chelates and the method by which they are absorbed is found below and is also documented in Ashmead et al., U.S. Pat. No. 4,863,898 which issued Sep. 5, 1989 and also in Ashmead et al., *Intestinal Absorption of Metal Ions and Chelates,* Published by Charles C. Thomas, Springfield, Ill., 1985.

DETAILED DESCRIPTION OF THE INVENTION

As documented by the Ashmead et al. publication, referenced above, mineral absorption from the intestinal tract occurs via at least two pathways. A mineral salt, after ingestion is solubilized and ionized in the acid pH of the stomach. The metal cations passing from the stomach into the intestinal tract are absorbed, if at all, in the duodenum or upper portion of the small intestine. This requires a relatively low acid pH. It is believed that the metal cation is presented to the integral proteins in the brush border of mucosal cells of the duodenum. The transport of the metal ion across the mucosal cell membrane is accomplished by chelating or complexing the cation to complex carrier proteins. This binding commences the activation of an enzymatic system called a "pump". Several enzyme reactions occur in which the cation is moved from molecule to molecule within the system. This movement is very rapid and stops when the cation is delivered to the interior side of the mucosal membrane where the metal cation is released and rechelated by cytoplasmic proteins, such as apoferritin, in the case or iron; ceruloplasmin in the case of copper; transmanganin in the case of manganese and albumin in the case of zinc and chromium. Other cytoplasmic proteins, such as siderophilin, may also involved in the case of chromium. The cation chelated with cytoplasmic protein is then carried to the basement membrane of the mucosal cell. Metal ions absorbed in this manner are reacted, released, re-reacted and re-released repeatedly during this transport from the intestinal tract to the portal blood.

Metal cations which are not absorbed via the duodenum descend on through the intestine to where the pH is increased. As the pH increases, the metal ions lose their soluble characteristics and react with phytates, phosphates, hydrophides and other anions to form insoluble precipitates which pass through the gut and are excreted in the feces.

The Ashmead et al. publication documents that when an impermeant substance, such as a metal cation is chemically linked to an amino acid or low molecular weight peptide, the resulting complex can be transported via a peptide transport system across the cell membrane. This has been referred to as having the impermeant substance "smuggled" across the membrane and the complex has accordingly been referred to in the literature as a "smugglin". These are the amino acid chelates above referred to having a ligand to mineral ratio of at least 1:1 and preferably 2:1 or greater, a molecular weight of no more than 1500 and preferably not more than 1000 and a stability constant of between about $10^6$ and $10^{16}$. In the field of animal nutrition, the American Association of Feed Control Officials has issued the following official definition: "amino acid chelate—a metal ion from a soluble salt with amino acids with a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800." It is also documented that amino acid chelates can be prepared from metal ions which do not come from soluble salts. Ashmead, U.S. Pat. No. 4,599,152 and Ashmead, U.S. Pat. No. 4,830,716 both disclose methods of preparing pure amino acid chelates using metal sources other than soluble metal salts. However, it is not critical to the present invention which manner the amino chelates are made provided they meet the criteria stated above.

While it is known that nutrition plays an important role in proper cellular physiology and maintenance of the overall health of humans and other members of the animal kingdom, it is probably the least understood factor in cellular biology. Researchers are just beginning to understand that trace element nutrition, or malnutrition as the case may be, is often the core of symptoms of stress. In cases of stress, chromium is essential to overall health and maintenance of the body. However, the content of total chromium administered in a diet may bear little relationship to its effectiveness if the form of the chromium is not bioavailable. Inorganic chromium salts are poorly absorbed. GTF from Brewer's yeast is much more bioavailable and hence effective. Chromium amino acid chelates are at least as, if not more, effective than GTF Brewer's years in providing bioavailable chromium.

Moreover, if manganese, zinc, iron, selenium and copper are also deficient, the immune system may be deficient. Even if these trace minerals are present in sufficient amounts in the diet, an overabundance of certain other trace minerals can interfere with their absorption. See, for example, Miller, *Trace Minerals-Role of Zinc, Iron and Selenium in Swine Immunity*"Feed Management Vol 40, pp 20, 1989. Also, as referenced above, the form of the nutrient is often more important than the quantity. Elemental salts are not as bioavailable as the amino acid chelates referred to, particularly when there is interference from heavy metals. If the immune system is not functioning properly, many of the drugs and/or methods relied on to treat and prevent disease are ineffectual and mortality may result.

Because, in addition to chromium, copper, zinc, manganese, iron and selenium are minerals of greatest concern and have a direct impact on maintaining the immune system and because stress has such an impact on depressing the immune system these are the minerals which are preferably formulated along with chromium. Besides being present in adequate quantities, the interrelationship of one mineral to another is important. Specific minerals may be present in adequate amounts according to assays. However, due to interference or competition, such minerals may not be biologically available or in proper balance. For example, it is known that excess molybdenum directly ties up copper. Manganese and iron compete for active ionic absorption sites in the small intestine. Manganese is readily excreted from the body, but there is no similar excretion mechanism for excess iron accumulation which also has an inhibitory affect on copper utilization.

The amino acid compositions will preferably be administered to humans or other warm blooded animal orally. In many cases mixtures of the chelates in the food, drinking water or other ration form given to the animal may be used. For example, the chelates may be mixed with salt (sodium chloride) when being administered to the bovine species. They may similarly be mixed with feed or rations destined for general animal or livestock usage. In the case of humans, the chelates may be administered in the form of tablets, capsules, powders, syrups, elixirs or any other suitable form. They may be mixed with fillers, excipients, vitamins and other foodstuffs.

The exact amount of mineral to be administered, and the ratio of one mineral to another, will depend upon animal species and the degree or particular form of stress anticipated and/or displayed by symptoms. Often, assay results of samples of tissue, serum or other body fluid may have to be taken before a proper formulation can be made. For example, the serum cortisol level may be a good indicator as to the amount of chromium to administer. To make a determination, the correct interpretation of data may be more important than the actual numbers generated in an assay and values must be correlated to bioavailability and antagonistic parameters of one trace element to another or from one trace element to other minerals such as copper and iron. An assay of the diet may also be important to determine mineral amounts in the diet and identify deficiencies and/or antagonistic factors which may affect trace minerals when administered.

Therefore, the exact amount of amino acid chelate, which minerals, in addition to chromium, to use and in what ratios, are preferably determined on an empirical basis according to need. Hence, the term, "effective amount" of one or more minerals is based on both the amount of mineral and the ratio of one mineral to another which has been determined to be required to meet the needs of a particular warm-blooded animal or group of animals, including humans, exhibiting certain symptoms of stress or to be subjected to conditions of stress. In some instances, based on collected data over periods of time, it will be possible to pre-formulate compositions based on known needs of the animal species which are subjected to certain forms of stress. However, one skilled in the art, based on the information provided herein, can determine without undue experimentation what an "effective amount" of a composition is and how to administer it accordingly. It is not possible to categorically state that "x" mg of trace mineral per kg of animal body weight is what is needed to prevent or alleviate stress. Nor is it possible to state, for example, that the amount of chromium to be administered will always be x mg/kg body weight or that, if used, the ratio of Cu to Zn will be "a:b" in all instances. Each animal species and form or conditions of stress may require different amounts of minerals and/or ratios of minerals. The type and/or magnitude of stress may also affect the "effective amount". For these reasons, a data bank of chromium and various other trace mineral levels and ratios which are found in various forms of stress according to animal species and a comparison these data against mineral levels and ratios found in healthy animals of the same species is being compiled. From these data the "effective amounts" of minerals to administer will be available. For animal species in which an RDA [recommended daily allowance], or similar nutritional guideline, has been established, that amount may be used as a minimum or threshold "effective" amount to be administered to that species. However, in some instances, it may be possible to administer even lesser amounts which are also "effective" provided the correct mineral ratios are used. Furthermore, an RDA supposes to examine all sources of a mineral ingested by the host. In the present invention, supplementation will be in addition to that contained in food sources. Therefore, an "effective amount" of a mineral may be administered consisting less than an established RDA. If the mineral ingested is considered in all forms, i.e. foods, supplements, etc., the total amount of mineral administered, in amino acid chelated form, and as other organic or chelated forms and inorganic forms, may actually exceed an RDA. Although no RDA for chromium has been established, at least one report, Polansky et al., supra, states that the minimum suggested daily chromium intake for adult human beings should be about 50 μg. It is believed that the amounts of chromium to be administered will be somewhat similar to those allowed for other trace microminerals such as selenium. Allowable amounts of selenium, given in 21 C.F.R. §573.920 for animals other than humans, are stated in terms of both ppm permissible in food or food supplements and milligrams/head/day as dosages for stated animal species. In general these amounts vary from between about 0.3 to 120 ppm for food or food supplements to provide an intake of up to about 3 milligrams/animal/day. U.S. Pat. No. 4,923,855 states that GTF materials may be formulated for human consumption to provide chromium in amounts ranging from as little as 4 μg/day up to 1000 μg/day. For cattle, horses or other large animals, chromium supplementation could be 10 mg/day or even higher. For purposes of this invention and "effective amount" could range from administering food compositions or supplements containing anywhere from about 0.05 to 150 ppm to provide dosages which could range anywhere between about 1 μg up to about 10 mg per day depending upon the animal species and conditions of stress being treated or anticipated. When formulated in dosage unit form in tablets, capsules, and the like, the concentration will obviously be higher than when formulated in food.

The following examples are illustrative of the invention showing treatment of warm-blooded animals suffering from symptoms of stress wherein these symptoms are alleviated or removed through the administration of chromium as an amino acid chelate. Formulations containing other trace minerals in amino acid chelate form is also shown.

EXAMPLE 1

Seventy two crossbred steer calves, averaging 234 kg live weight and were obtained from two different feeder sales in the late autumn. These calves, having recently been weaned and transported, showed conventional symptoms of weaning/marketing stress, i.e. weight loss, loss of appetite, etc. The calves were weighed upon arrival, treated with Ivomec and randomly assigned into four groups, each containing 18 calves. Calves in each group were further divided into pens containing three calves per pen. The calves in each group were given different trace mineral supplementations during the first seven days. Group 1 was a control with no supplementation. Group 2 received a high chromium yeast (Brewer's yeast), Group 3 received amino acid chelated chromium and Group 4 received amino acid chelated chromium, copper, zinc and manganese. The chromium was supplemented at a level of 4.0 mg/calf/day. When given, zinc and copper was supplemented at 120 mg/calf/day, and manganese at 50 mg/calf/day. All amino acid chelates were within the ligand to metal ratios and molecular weight and stability constant ranges stated above.

During the first week, the supplement was added as a water suspension sprinkled onto a small amount of chopped hay fed once daily prior to feeding silage. This ensured adequate and uniform consumption of chromium and, when added, other minerals animal.

Following the first week, only chromium was supplemented at 0.5 ppm in diet dry matter. The calves in each group were weighed on days 21 and 35 after a fast of 24 hours for feed and 16 hours for water. Blood samples were obtained from each animal by jugular puncture at days 0, 14 and 34. Serum was analyzed for glucose and cortisol. The animals were watched closely for symptoms of BRD, particularly if they were off feed or exhibited rapid breathing, depression and/or gauntness. If the rectal temperature was greater than or equal to 40.0° C., they were treated with Liquamycin L.A. A few steers showing severe signs of rapid breathing or depression were placed on antibiotic treatment even though there temperature was below 40.0° C. Results are given in following Table 1:

TABLE 1

| | Group Number | | | |
|---|---|---|---|---|
| | 1[a] | 2[b] | 3[c] | 4[d] |
| No. Calves | 18 | 17* | 18 | 18 |
| Initial Average Live Weight (Kg) | 238 | 228 | 237 | 231 |
| Occurrence Morbidity (%) | 55.5 | 33.3 | 11.1 | 22.2 |
| Onset of Morbidity (%) | | | | |
| Day 0–9 | 5.5 | 11.1 | 0 | 0 |
| Day 10–14 | 16.7 | 16.7 | 5.5 | 5.5 |
| Day 15–19 | 50.0 | 33.3 | 16.1 | 11.6 |
| Day 20–25 | 55.5 | 33.3 | 16.6 | 16.6 |
| Ave. Daily Wt. Gain (Kg) | | | | |
| Day 0–21 | | | | |
| Healthy | .72 | .64 | .67 | .63 |
| Morbid | .19 | .08 | .33 | .43 |
| Overall | .42 | .46 | .62 | .58 |

TABLE 1-continued

| | Group Number | | | |
|---|---|---|---|---|
| | 1[a] | 2[b] | 3[c] | 4[d] |
| Day 21–35 | | | | |
| Healthy | .80 | 1.06 | .82 | 1.00 |
| Morbid | 1.02 | 1.10 | .80 | 1.24 |
| Overall | .92 | 1.08 | .82 | 1.06 |
| Day 0–35 | | | | |
| Healthy | .75 | .81 | .73 | .78 |
| Morbid | .52 | .49 | .52 | .75 |
| Overall | .62 | .71 | .70 | .77 |
| Dry Matter Intake (kg/day) | | | | |
| Week One | 3.32 | 3.47 | 3.59 | 3.50 |
| Week Two | 4.28 | 4.44 | 4.67 | 4.72 |
| Week Three | 3.29 | 3.39 | 4.10 | 3.64 |
| Week Four | 4.60 | 4.76 | 5.12 | 5.20 |
| Week Five | 4.62 | 4.58 | 4.55 | 4.82 |
| Overall Average | 4.02 | 4.13 | 4.41 | 4.38 |

[a]Control, no chromium supplementation
[b]Cr administered as high chromium Brewer's yeast
[c]Cr administered as chromium amino acid chelate
[d]Cr, Zn Cu and Mn administered as amino acid chelates (Zn, Cu and Mn administered first week only)
*One calf died during test period The above data clearly demonstrate that supplementation of chromium, particularly when administered in amino acid chelated form, significantly reduces the onset of morbidity, by reducing the effects of stress and strengthening the immune system of the animal. While high chromium yeast tended to also reduce morbidity, it was not as effective as the amino acid chelated chromium. The morbidity of the chelated chromium treated groups was less than one third of the control and no treated animals relapsed, died or failed to respond to treatment.

The chromium treated groups showed both better weight gain and food consumption than the control group. Also, the groups treated with amino acid chelated chromium showed higher food consumption, an indicator of reduced stress, and comparable or better weight gain, particularly with morbid animals in early stages of morbidity.

The results of this test shows that chromium supplementation may be as effective as antibiotic treatment in weight gain and reducing effects of stress in animals subjected to weaning/marketing stress. Clearly chromium supplementation, as a prophylactic, would be preferable to antibiotic treatment in reducing morbidity, improving weight gain and otherwise countering the effects of stress.

EXAMPLE 2

In this Example the supplemental chromium was derived from high chromium yeast. The results demonstrate that chromium supplementation will reduce serum cortisol and glucose levels. Charolais-crossed calves, weighing on the average of 245 kg following transportation from a several hundred mile distance, were allotted to one of four treatment groups during an initial 28 day stress period. One group was a control, the second received 0.4 ppm chromium in their feed, the third received a long-acting injectable oxytetracycline (LA) 48 hours after arrival and the fourth received the LA injections plus chromium supplementation at 0.4 ppm in their feed. Those fed chromium also received 4 mg of chromium per day for the first three days sprinkled onto a small amount of hay over the silage feed. Chromium supplementation had a positive effect comparable to antibiotic supplementation on weight gain but was not as efficient in reducing the onset of morbidity.

After the initial 28 day period, the calves were vaccinated with IBR/PI$_3$, injected with Ivomec and dehorned. Two weeks later, the calves were re-randomized into four groups for a 70 day growing period. The basic diet fed was corn silage which was supplemented with either urea or soy bean meal (SBM). Two groups of eight calves each was a control with one group receiving the urea and the other group the SBM supplement. Two other groups, were given the same diet supplemented with 0.2 ppm chromium from GTF Brewer's yeast. On two occasions during the period blood samples were collected from the jugular vein and analyzed for cortisol, glucose and a variety of other items including immunoglobulins. The average results of both samplings, as they relate to serum cortisol and glucose are given in Table 2:

TABLE 2

|  | Control | | Chromium | | Chromium/Control | |
| --- | --- | --- | --- | --- | --- | --- |
|  | Urea | SBM | Urea | SBM | Urea | SBM |
| Cortisol (nmol/L) | 89.38 | 60.63 | 64.38 | 46.88 | 0.72 | 0.77 |
| Glucose (mmol/L) | 5.31 | 4.88 | 5.01 | 4.72 | 0.94 | 0.97 |

Serum cortisol was significantly decreased (38 and 33% respectively) and a reduction of serum glucose was noted in each test. These results clearly indicate that chromium supplementation will decrease serum cortisol levels and are an indication that the immune status of the recipients is improved.

EXAMPLE 3

A test similar to that given in Example 2 was repeated using chromium amino acid chelate in the place of GTF chromium from Brewer's yeast. This form of chromium was administered only at 0.1 ppm in the feed instead of the 0.2 ppm used in Example 2. Serum cortisol and glucose levels from two replicates from six calves are given in Table 3:

TABLE 3

|  | Control | Chromium | Chromium/Control |
| --- | --- | --- | --- |
| Cortisol (nmol/L) | 70.67 | 37.08 | 0.53 |
| Glucose (mmol/L) | 5.02 | 4.50 | 0.89 |

The results in this test show that cortisol levels in the chromium amino acid chelate group were reduced by 47% and glucose levels were decreased over 10% over the control group when the steers were fed a diet containing 0.1 ppm of chromium amino acid chelate. This is markedly superior to the results obtained when using a chromium obtained from Brewer's yeast.

While the above provides a detailed description of the invention and the best mode of practicing it to the extent that it has been developed, the invention is not to be limited solely to the description and examples. There are modifications which may become apparent to one skilled in the art in view of the description contained herein. Therefore, the invention is to be limited in scope only by the following claims and their functional equivalents.

We claim:

1. A method for alleviating stress in a warm-blooded animal which comprises the steps:
    (a) providing a composition containing an effective amount of chromium in the form of an amino acid chelate having a ligand to mineral ratio of at least 1:1, a molecular weight of no more than 1500 and a stability constant of between about $10^6$ and $10^{16}$ and
    (b) administering said composition to said warm-blooded animal.

2. A method according to claim 1 wherein said ligand to mineral ratio is 2:1 or greater.

3. A method according to claim 2 wherein said chelate has a molecular weight no greater than about 1000.

4. A method according to claim 3 wherein said composition is administered orally.

5. A method according to claim 4 wherein said composition is administered in the food of said animal.

6. A method according to claim 5 wherein said composition is continuously available to said animal.

7. A method according to claim 4 wherein said composition is administered in unit dosage form.

8. A method according to claim 4 wherein said composition is administered in response to said animal showing symptoms of stress.

9. A method according to claim 4 wherein said composition is administered as a prophylactic.

10. A method according to claim 4 wherein said chromium is administered in amounts to provide a dosage of between about 1 μg to 10 mg per day.

11. A method for alleviating stress in a warm-blooded animal which comprises the steps:
    (a) providing a composition containing an effective amount of chromium, and, at least one other mineral selected from the group consisting of copper, zinc, manganese, iron and selenium, wherein said chromium and such other mineral is in the form of an amino acid chelate having a ligand to mineral ratio of at least 1:1, a molecular weight of no more than 1500 and a stability constant of between about $10^6$ and $10^{16}$ and
    (b) administering said composition to said warm-blooded animal.

12. A method according to claim 11 wherein said ligand to mineral ratio is 2:1 or greater.

13. A method according to claim 12 wherein said chelate has a molecular weight no greater than about 1000.

14. A method according to claim 13 wherein said composition is administered orally.

15. A method according to claim 14 wherein said composition is administered in the food of said animal.

16. A method according to claim 15 wherein said composition is continuously available to said animal.

17. A method according to claim 14 wherein said composition administered in unit dosage form.

18. A method according to claim 14 wherein said composition is administered in response to said animal showing symptoms of stress.

19. A method according to claim 14 wherein said composition administered as a prophylactic.

20. A method according to claim 14 wherein said chromium is administered in amounts to provide a dosage of between about 1 μg to 10 mg per day.

* * * * *